(12) United States Patent
Damle et al.

(10) Patent No.: US 11,813,252 B2
(45) Date of Patent: Nov. 14, 2023

(54) TREATMENT FOR PARKINSON'S DISEASE

(71) Applicant: SUN PHARMA ADVANCED RESEARCH COMPANY LTD., Mumbai (IN)

(72) Inventors: Nitin Krishnaji Damle, Mumbai (IN); Sanjay Nandlalji Mandhane, Baroda (IN); Manoj Atmaramji Upadhya, Baroda (IN); Sameer Vishwanath Mehetre, Baroda (IN); Gajanan Uttamrao Chidrewar, Baroda (IN); Prabal Sengupta, Baroda (IN); Trinadha Rao Chitturi, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

(21) Appl. No.: 17/747,472

(22) Filed: May 18, 2022

(65) Prior Publication Data

US 2022/0273632 A1 Sep. 1, 2022

Related U.S. Application Data

(63) Continuation of application No. 17/061,139, filed on Oct. 1, 2020, now Pat. No. 11,583,522, which is a continuation of application No. 16/304,914, filed as
(Continued)

(30) Foreign Application Priority Data

Jun. 2, 2016 (IN) .............................. 201621019087
Jun. 2, 2016 (IN) .............................. 201621019185

(51) Int. Cl.
*A61K 31/44* (2006.01)
*A61P 25/16* (2006.01)
*A61K 31/47* (2006.01)

(52) U.S. Cl.
CPC .............. *A61K 31/44* (2013.01); *A61K 31/47* (2013.01); *A61P 25/16* (2018.01)

(58) Field of Classification Search
CPC ......... A61K 31/44; A61K 31/47; A61P 25/16; A61P 43/00
(Continued)

(56) References Cited

U.S. PATENT DOCUMENTS 10,849,887 B2  12/2020  Damle et al.

FOREIGN PATENT DOCUMENTS

WO  2012/098416 A1  7/2012
WO  2016/185490 A1  11/2016

OTHER PUBLICATIONS

Imam et al., Neuroprotective Efficacy of a New Brain Penetrating C-Abl Inhibitor in a Murine Parkinson's Disease Model, 2013 PLOS ONE, vol. 8, Iss. 5, e65129, pp. 1-8 (Year: 2013).
(Continued)

*Primary Examiner* — Taylor V Oh
(74) *Attorney, Agent, or Firm* — Sughrue Mion, PLLC

(57) ABSTRACT

The invention relates to a method of treating or preventing Parkinson's disease in a subject comprising administering a compound of Formula I Formula I (Continued)

wherein, $R_1$ is —NHC(O) $C_{3-6}$ cycloalkyl and $R_2$ is hydrogen;

or $R_1$ and $R_2$ along with the carbon atoms to which they are attached form a six membered aromatic ring, wherein the ring is substituted with one or more groups selected from hydrogen, halogen and $C_{1-6}$ alkyl;

$R_3$ and $R_4$ are independently selected from group comprising hydrogen, halogen, $C_{1-3}$ alkyl, $OC_{1-3}$ alkyl, $NO_2$, $SC_{1-3}$ alkyl, $C_{1-3}$ haloalkyl, $OC_{1-3}$ haloalkyl, and $SC_{1-3}$ haloalkyl; or a pharmaceutically acceptable salt thereof.

4 Claims, 6 Drawing Sheets

Related U.S. Application Data application No. PCT/IN2017/050224 on Jun. 2, 2017, now Pat. No. 10,849,887.

(58) Field of Classification Search
USPC .......................................................... 514/313
See application file for complete search history.

(56) References Cited

OTHER PUBLICATIONS

International Search Report for PCT/IN2017/050224, dated Sep. 26, 2017.

Karuppagounderetal., The c-Abl inhibitor, Nilotinib, protects dopaminergic neurons in a preclincal animal model of Parkinson's disease, 2014, Nature: Scientific Reports, 4:4874, pp. 1-8 (Year: 2014).

Written Opinion for PCT/IN2017/050224, dated Sep. 26, 2017.

Fig 1. Photomicrographs from coronal sections showing tyrosine hydroxylase (TH)-positive neurons
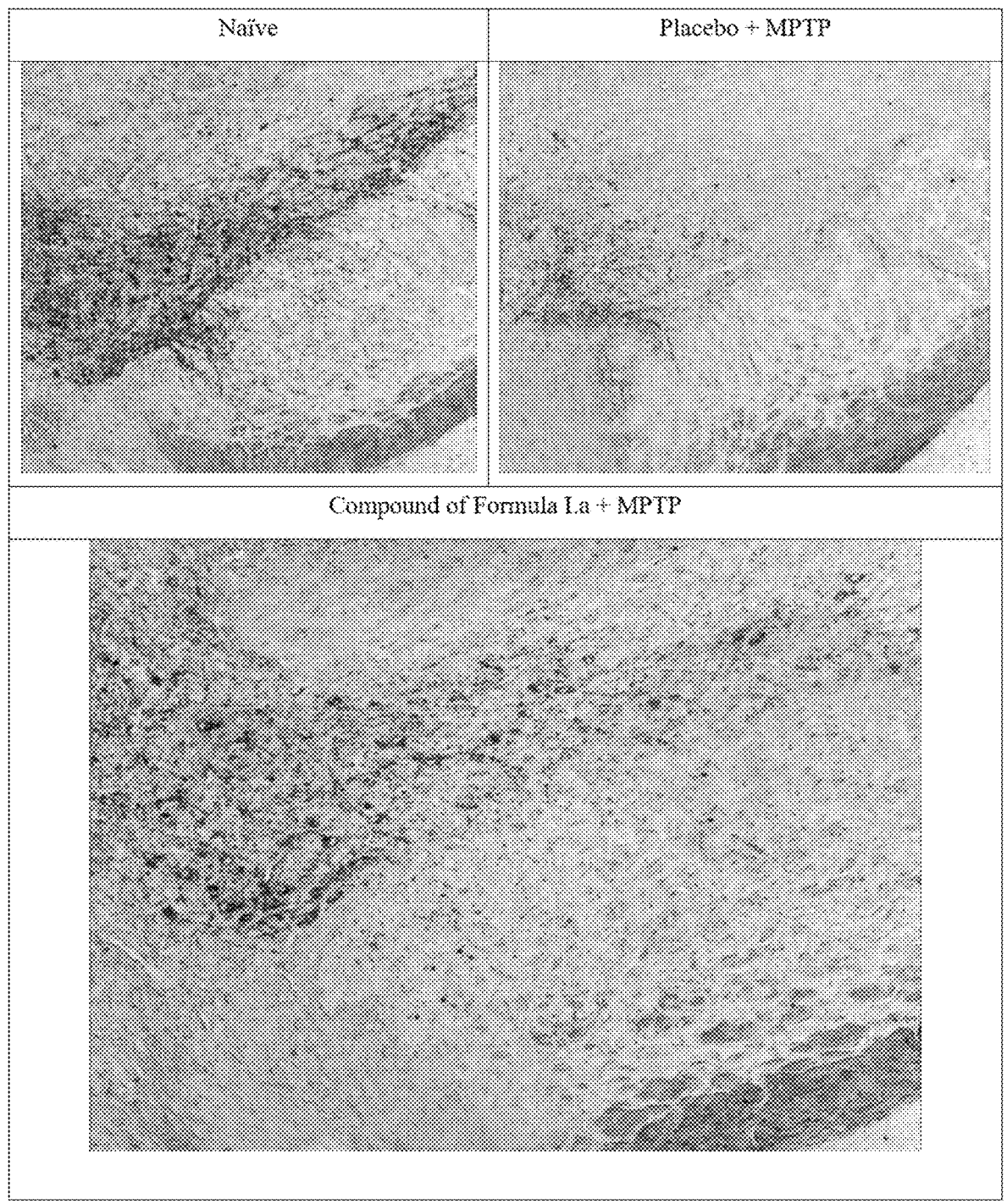

Fig. 2. Percentage area of TH-positive neurons on administration of the compound of Formula I.a.
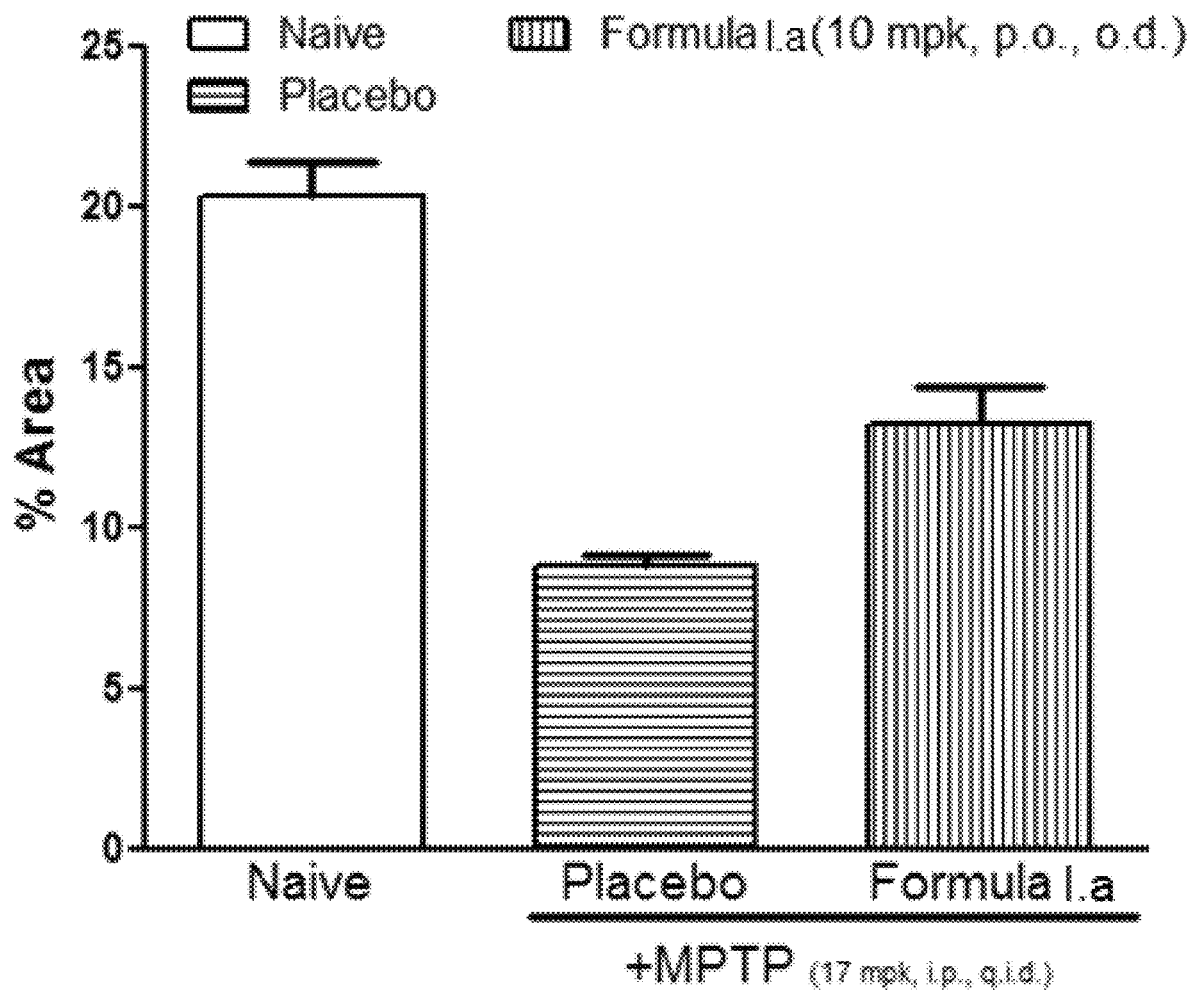

Fig. 3. Integrated density of TH-immunoreactivity on administration of the compound of Formula I.a and nilotinib.
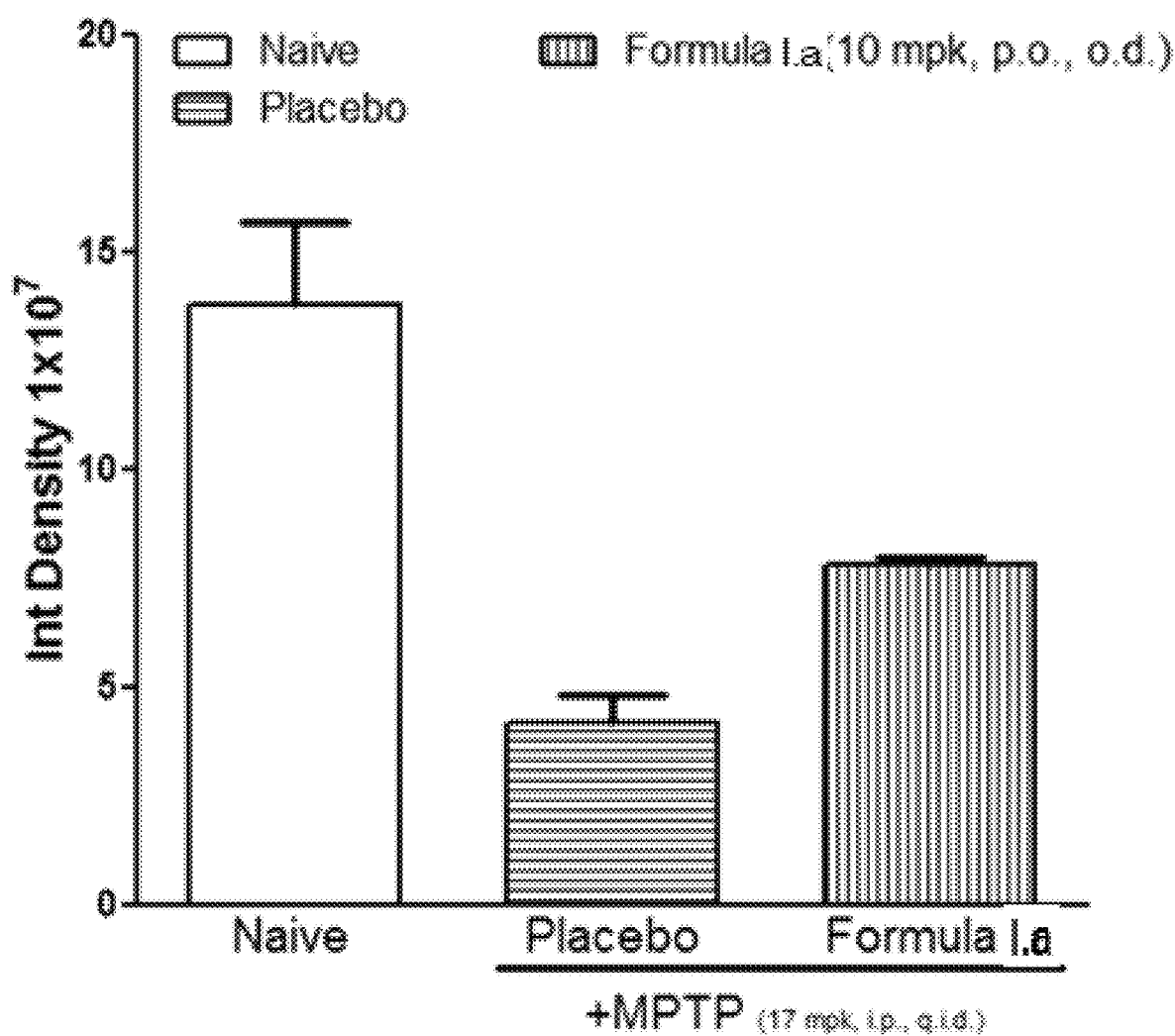

Fig 4. Photomicrographs from coronal sections showing tyrosine hydroxylase (TH)-positive neurons
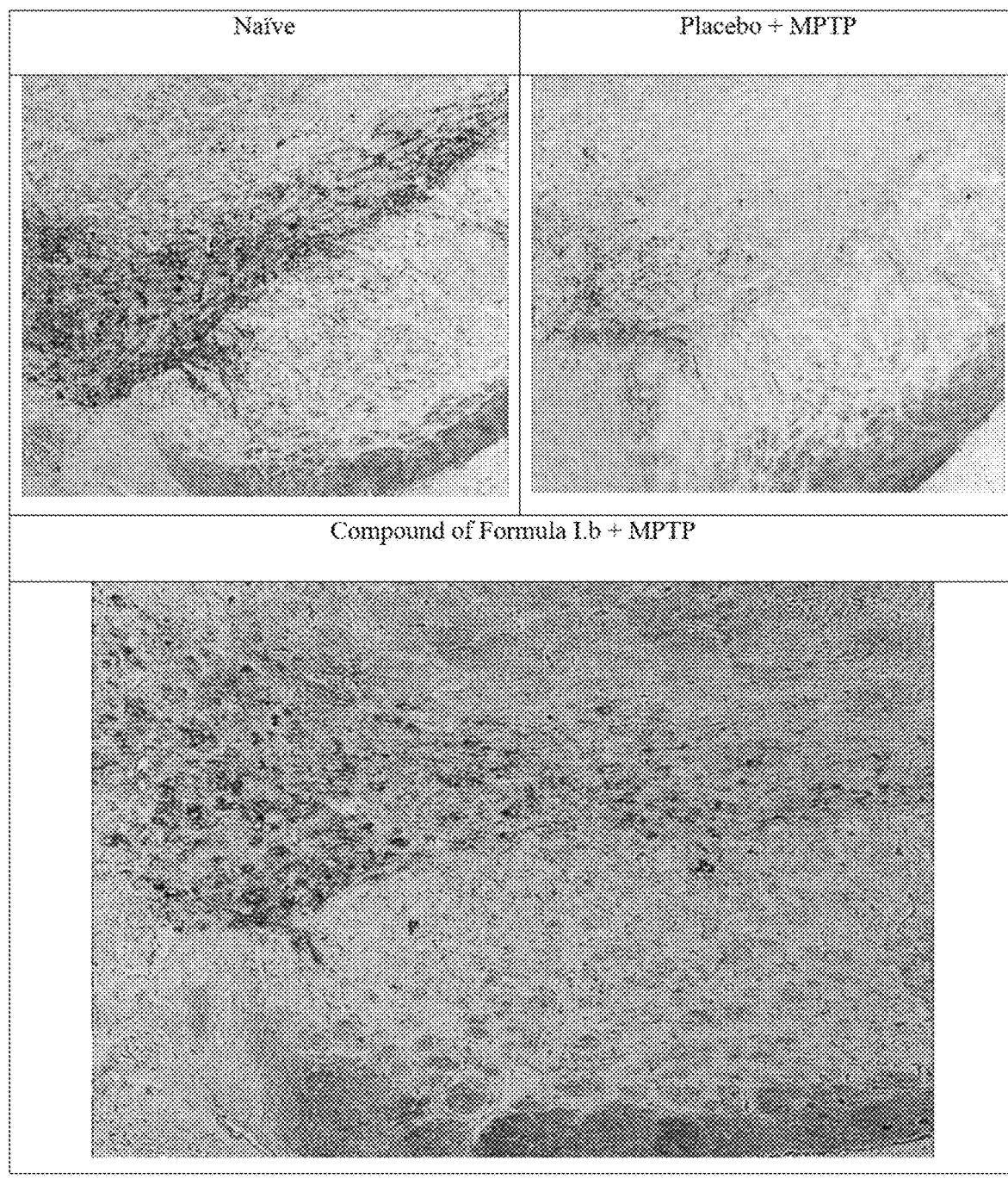

Fig. 5. Percentage area of TH-positive neurons on administration of the compound of Formula I.b.
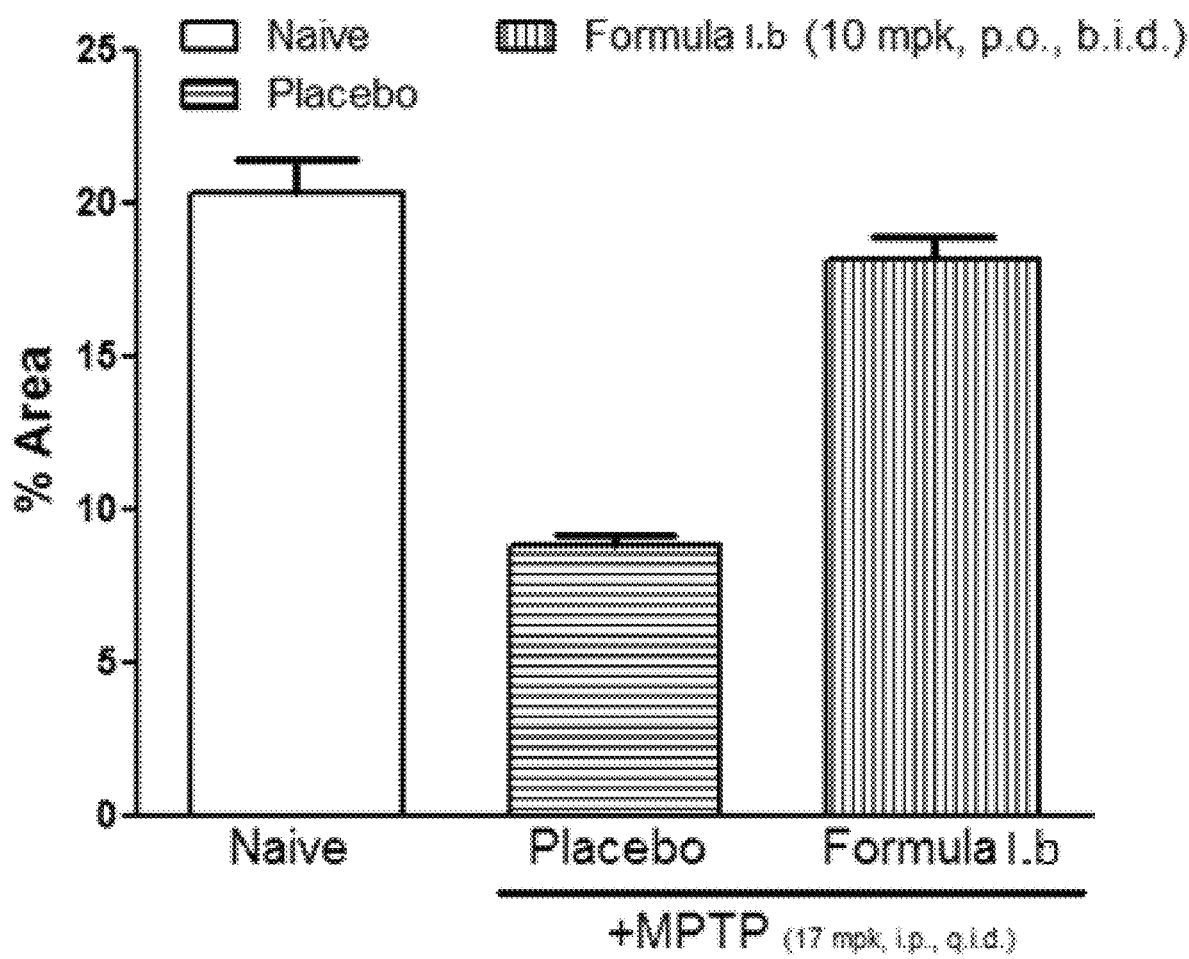

Fig. 6. Integrated density of TH-immunoreactivity on administration of the compound of Formula I.b and nilotinib.
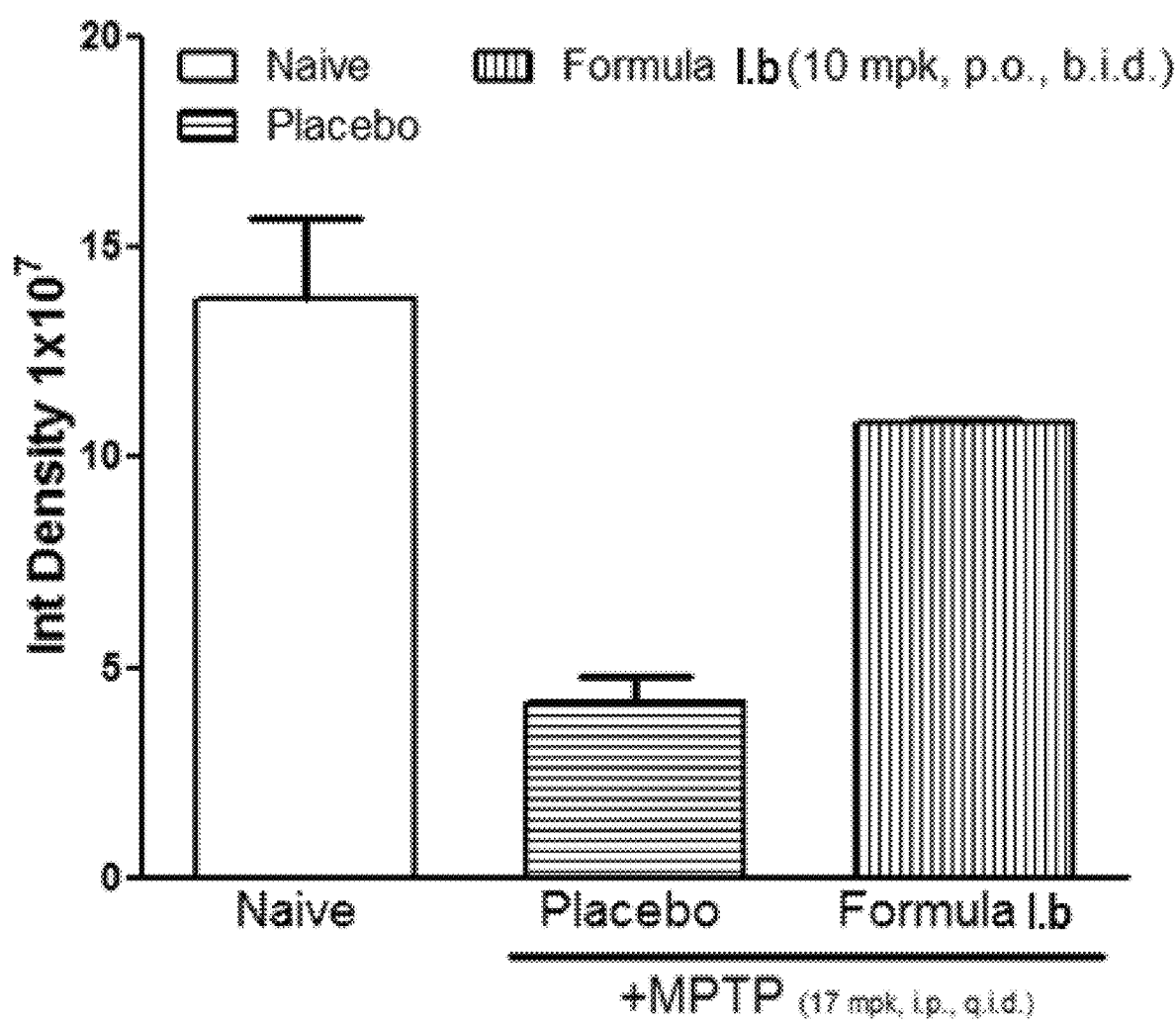

TREATMENT FOR PARKINSON'S DISEASE

CROSS-REFERENCE TO RELATED APPLICATION

This application is a Continuation of U.S. application Ser. No. 17/061,139, filed Oct. 1, 2020, which is a Continuation of U.S. application Ser. No. 16/304,914, filed Nov. 27, 2018, now U.S. Pat. No. 10,849,887, issued on Dec. 1, 2020, which is a National Stage Entry of PCT/IN2017/050224 filed on Jun. 2, 2017, which claims priority from Indian Patent Application no. IN 201621019087 filed on Jun. 2, 2016 and IN 201621019185 filed on Jun. 2, 2016, the contents of all of which are incorporated herein by reference, in their entirety.

FIELD OF THE INVENTION

The invention relates to a method of treating or preventing Parkinson's disease in a subject comprising administering a compound of Formula I

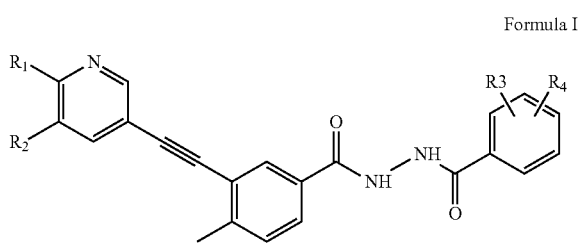

Formula I wherein, $R_1$ is —NHC(O) $C_{3-6}$ cycloalkyl and $R_2$ is hydrogen;

or $R_1$ and $R_2$ along with the carbon atoms to which they are attached form a six membered aromatic ring, wherein the ring is substituted with one or more groups selected from hydrogen, halogen and $C_{1-6}$ alkyl;

$R_3$ and $R_4$ are independently selected from group comprising hydrogen, halogen, $C_{1-3}$ alkyl, $OC_{1-3}$ alkyl, $NO_2$, $SC_{1-3}$ alkyl, $C_{1-3}$ haloalkyl, $OC_{1-3}$ haloalkyl, and $SC_{1-3}$ haloalkyl; or a pharmaceutically acceptable salt thereof.

BACKGROUND OF THE INVENTION c-Abl is a non-receptor protein tyrosine kinase that is implicated in various cellular processes which include regulation of cell survival, growth and motility. c-Abl kinase inhibitors such as imatinib (Gleevec®), nilotinib (Tasigna®), dasatinib (Sprycel®) and ponatinib (Iclusig®) have been developed and marketed for clinical use in the treatment of chronic myeloid leukemia.

Recent studies have demonstrated that c-Abl plays an important role in oxidative stress-induced neuronal cell death (Wu et al., Cell Death Differ., 2016; 23:542-552). It has been reported that c-Abl is involved in Parkinson's disease (Gonfloni et al., Int. J. Cell Biol., 2012; 2012:1-7). Also, c-Abl is known to be activated by dopaminergic stress and by dopaminergic neurotoxins viz. 1-methyl-4-phenyl-1, 2,3,6-tetrahydropyridine (MPTP, converted enzymatically in vivo to its active form $MPP^+$) causes tyrosine phosphorylation of parkin leading to loss of parkin's E3 ligase activity. This results in the accumulation of various substrates of parkin and ultimately to death of dopaminergic neurons (Ko et al., PNAS, 2010; 107:16691-16696).

Parkinson disease (PD) is a common neurodegenerative disease characterized by protein accumulation in intracellular inclusions designated as Lewy bodies and Lewy neuritis and subsequent loss of dopaminergic neurons. Rare familial mutations have provided insight into this chronic, progressive neurodegenerative disease like mutation in α-synuclein and LRRK2 cause autosomal-dominant PD, whereas mutations in DJ-1, PINK1 and parkin results in autosomal-recessive PD. Parkin is an E3 ubiquitin ligase, and familial mutations are thought to impair E3 ligase activity of parkin (Ko et al., PNAS, 2010; 107:16691-16696).

c-Abl has been shown to regulate the degradation of two proteins implicated in the pathogenesis of PD viz. parkin and α-synuclein (Mahul-Mellier et al., Hum. Mol. Genet., 2014; 23:2858-2879). c-Abl phosphorylates parkin on tyrosine 143. This phosphorylation inhibits parkin's E3 ubiquitin ligase activity, leading to accumulation of AIMP2 and FBP1 (parkin substrates) and loss of parkin's cytoprotective function resulting in cell death (Ko et al., PNAS, 2010; 107: 16691-16696; Imam et al., J. Neurosci., 2011; 31:157-163). Further, c-Abl regulates clearance of α-synuclein, a synaptic protein that has been strongly implicated in the pathogenesis of PD. A bi-directional relationship in vivo between α-synuclein and c-Abl has been described wherein an increase in α-synuclein expression facilitates its phosphorylation and subsequent activation of c-Abl. Conversely, an increase in the c-Abl expression and activation results in α-synuclein accumulation and aggregation, suggesting that inhibition of c-Abl might constitute a viable strategy for protecting dopaminergic neurons from accumulated α-synuclein toxicity in PD (Hebron et al., Hum. Mol. Genet., 2013; 22:3315-3328; Hebron et al., Autophagy, 2013; 9:1249-1250).

c-Abl inhibitors like nilotinib are known to cross the blood-brain barrier and protect dopaminergic neurons in a mouse model of PD induced with 1-methyl-4-phenyl-1,2,3, 6-tetrahydropyridine (herein referred to as MPTP) (Karuppagounder et al., Sci. Rep. 2014; 4:4874). Nilotinib has been shown to increase α-synuclein clearance via the autophagy pathway and protects against α-synuclein accumulation-induced loss of dopaminergic neurons in this mouse model of PD (Hebron et al., Hum. Mol. Genet., 2013; 22:3315-3328; Imam et al., J. Neurosci., 2011; 31:157-163). Further, US20150087653 discloses method of treating neurodegenerative diseases comprising of administering tyrosine kinase inhibitors such as nilotinib. However, nilotinib has several major drug associated adverse effects. USFDA has issued a boxed warning for Tasigna® capsules since its treatment is associated with potentially severe cardiac side effects (QT prolongation) and sudden deaths in patients. Dasatinib is known to cause pleural effusion and hemorrhage. Ponatinib is also associated with severe adverse effects which include thromboembolism and vascular occlusion. Imatinib is not a potent inhibitor of Abl kinase. Moreover, both imatinib and dasatinib being P-glycoprotein (p-gp) substrate, show poor brain concentration. Thus, there is a need for a potent Abl kinase inhibitor which can cross the blood-brain barrier and does not cause cardiovascular side effects.

SUMMARY OF THE INVENTION

The invention provides method of treating or preventing Parkinson's disease in a subject comprising administering a therapeutically effective amount of a compound of Formula I,

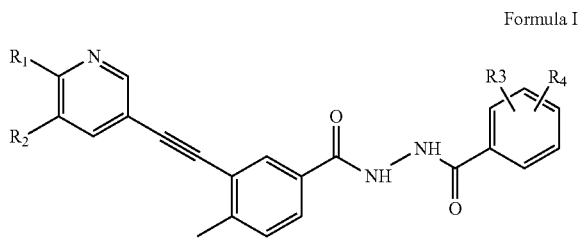

Formula I wherein, $R_1$ is —NHC(O) $C_{3-6}$ cycloalkyl and $R_2$ is hydrogen;

or $R_1$ and $R_2$ along with the carbon atoms to which they are attached form a six membered aromatic ring, wherein the ring is substituted with one or more groups selected from hydrogen, halogen and $C_{1-6}$ alkyl;

$R_3$ and $R_4$ are independently selected from group comprising hydrogen, halogen, $C_{1-3}$ alkyl, $OC_{1-3}$ alkyl, $NO_2$, $SC_{1-3}$ alkyl, $C_{1-3}$ haloalkyl, $OC_{1-3}$ haloalkyl, and $SC_{1-3}$ haloalkyl; or its pharmaceutically acceptable salt thereof.

DESCRIPTION OF THE FIGURES

FIG. 1. Photomicrographs from coronal sections showing tyrosine hydroxylase (TH)-positive neurons, showing prevention of neurodegeneration by the compound of Formula I.a.

FIG. 2. Percentage area of TH-positive neurons on administration of the compound of Formula I.a.

FIG. 3. Integrated density of TH-immunoreactivity on administration of the compound of Formula I.a.

FIG. 4. Photomicrographs from coronal sections showing tyrosine hydroxylase (TH)-positive neurons, showing prevention of neurodegeneration by the compound of Formula I.b.

FIG. 5. Percentage area of TH-positive neurons on administration of the compound of Formula I.b.

FIG. 6. Integrated density of TH-immunoreactivity on administration of the compound of Formula I.b.

DETAILED DESCRIPTION OF THE INVENTION

In one aspect, the present invention provides a method of treating or preventing Parkinson's disease in a subject comprising administering a therapeutically effective amount of the compound of Formula I,

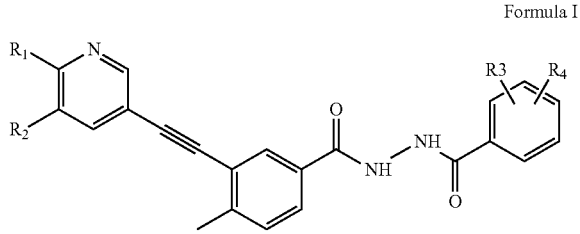

Formula I wherein, $R_1$ is —NHC(O) $C_{3-6}$ cycloalkyl and $R_2$ is hydrogen;

or $R_1$ and $R_2$ along with the carbon atoms to which they are attached form a six membered aromatic ring, wherein the ring is substituted with one or more groups selected from hydrogen, halogen and $C_{1-6}$ alkyl;

$R_3$ and $R_4$ are independently selected from group comprising hydrogen, halogen, $C_{1-3}$ alkyl, $OC_{1-3}$ alkyl, $NO_2$, $SC_{1-3}$ alkyl, $C_{1-3}$ haloalkyl, $OC_{1-3}$ haloalkyl, and $SC_{1-3}$ haloalkyl; or its pharmaceutically acceptable salt thereof.

In another aspect, the present invention provides a method of treating or preventing Parkinson's disease in a subject, comprising selecting a subject suffering from Parkinson's disease or at risk of developing Parkinson's disease and administering a therapeutically effective amount of a compound of Formula I.

The phrase "therapeutically effective amount of compound of Formula I" as used herein refers to amount of the compound of Formula I that elicit the therapeutic effect for which it is administered.

The term "alkyl" refers to a saturated hydrocarbon chain radical that includes solely carbon and hydrogen atoms in the backbone, either linear or branched and which is attached to the rest of the molecule by a single bond, e.g., methyl, ethyl, n-propyl, 1-methylethyl (isopropyl), n-butyl and n-pentyl.

The numerical in phrases like "$C_{1-6}$ alkyl", refers that there are 1 to 6 carbon atoms in the alky chain.

The term "$C_{3-6}$ cycloalkyl" refers to a non-aromatic mono-cyclic ring system of 3 to 6 carbon atoms. Monocyclic rings include cylcopropyl, cyclobutyl, cyclopentyl and cyclohexyl.

The term "haloalkyl" refers to alkyl chain substituted with one or more halogen radical selected from chloride, bromide, iodide and fluoride.

In one embodiment, the present invention provides method of treating or preventing Parkinson's disease comprising administering a therapeutically effective amount of a compound of Formula I wherein $R_1$ in the compound of Formula I is —NHC(O) cyclopropyl and $R_2$ is hydrogen.

In another embodiment, the present invention provides a method of treating or preventing Parkinson's disease comprising administering a therapeutically effective amount of a compound of Formula I wherein, $R_1$ and $R_2$ in the compound of Formula I, along with the carbon atoms to which they are attached form a six membered aromatic ring, wherein the ring is substituted with one or more groups selected from hydrogen, halogen and $C_{1-6}$ alkyl. Preferably, the aromatic ring is substituted with hydrogen i.e. unsubstituted.

In another embodiment, the present invention provides a method of treating or preventing Parkinson's disease comprising administering a therapeutically effective amount of a compound of Formula I wherein, $R_1$ and $R_2$ in the compound of Formula I, along with the carbon atoms to which they are attached form a six membered aromatic ring, wherein the ring is substituted with hydrogen i.e. unsubstituted; and $R_3$ is chloro and $R_4$ is methyl and are present as a substituent at 2 and 6 position in the ring.

In another embodiment, the present invention provides a method of treating or preventing Parkinson's disease comprising administering a therapeutically effective amount of a compound of Formula I wherein, $R_3$ and $R_4$ in the compound of Formula I are selected from halogen and $C_{1-6}$ alkyl. In a preferred embodiment, $R_3$ and $R_4$ are halogen and methyl and are present as a substituent at 2 and 6 position in the ring.

The chemical name of some of the preferred compounds of Formula I are provided below in Table 1.

TABLE 1

| Compound No. | Chemical name |
|---|---|
| I.a | N'-(2-Chloro-6-methylbenzoyl)-4-methyl-3-[2-(3-quinolyl)ethynyl]-benzohydrazide |
| I.b | Cyclopropanecarboxylic acid (5-{5-[N'-(2-chloro-6-methylbenzoyl)hydrazinecarbonyl]-2-methyl-phenylethynyl}-pyridin-2-yl)amide |
| I.c | Cyclohexanecarboxylic acid (5-{5-[N'-(2-chloro-6-methylbenzoyl)hydrazinecarbonyl]-2-methyl-phenylethynyl}-pyridin-2-yl)amide |
| I.d | Cyclobutanecarboxylic acid (5-{5-[N'-(2-chloro-6-methylbenzoyl)hydrazinecarbonyl]-2-methyl-phenylethynyl}-pyridin-2-yl)amide |
| I.e | N'-(2-Chloro-6-methylbenzoyl)-4-methyl-3-[2-(6-chloro-3-quinolyl)ethynyl]-benzohydrazide |
| I.f | N'-(2-Chloro-6-methylbenzoyl)-4-methyl-3-[2-(6-methyl-3-quinolyl)ethynyl]-benzohydrazide |
| I.g | N'-(2-Chloro-6-methylbenzoyl)-4-methyl-3-[2-(6-fluoro-3-quinolyl)ethynyl]-benzohydrazide |

Suitable pharmaceutically acceptable salts of the compound of the invention may be salts of inorganic acids such as hydrochloric acid, hydrobromic acid, phosphoric acid, and the like or of organic acids such as, for example, acetic acid, benzenesulfonic acid, methanesulfonic acid, benzoic acid, citric acid, glycolic acid, lactic acid, fumaric acid, succinic acid, adipic acid, pimelic acid, suberic acid, azelaic acid, malic acid, tartaric acid, or amino acids, such as glutamic acid or aspartic acid, and the like. One or more hydrogen atoms of the compound of Formula I may be deuterated i.e. substituted with a deuterium atom.

WIPO publication WO2012098416 (the '416 publication) discloses a markush group of compounds active as c-Abl kinase inhibitors and their usefulness for the treatment of cancers like chronic myelogenous leukemia (CML). Compounds of Formula I of the present invention may be prepared by the processes described in WO2012098416 and WO2016185490 which are incorporated herein by reference.

The inventors have found that the compound of Formula I of present invention, are potent Abl kinase inhibitors and advantageously cross the blood-brain barrier effectively resulting in a high ratio of brain to plasma concentration for the compound of Formula I and a high therapeutic index.

Particularly, the inventors have found that the compound of Formula I, at therapeutically effective dose, is devoid of cardiovascular side effects when tested for its in vitro effect on hERG channel and its in vivo effect on ECG parameters like QT interval, $QT_C$ interval, $QT_{cf}$ interval and heart rate in conscious beagle dogs and guinea pig. The compound of Formula I was found to be safe as they did not show any undue effect on ECG parameters and heart rate as described herein in examples.

The compound of Formula I can be administered orally in the form of a suitable dosage form. A suitable dosage form may include tablet, pellets, capsule, sachet, pellets in sachet, pellets in capsule, powder, granules and the like. The compound of Formula I may be formulated in oral dosage form which may include pharmaceutically acceptable excipients which are in common knowledge of a person skilled in the art. Remington's Pharmaceutical Sciences, Sixteenth Edition, E. W. Martin (Mack Publishing Co., Easton, Pa., 1980) discloses pharmaceutically acceptable carriers which can be used for preparation of a suitable dosage form.

The following examples serve to illustrate the invention without limiting the invention in its scope.

Example 1

Abl Kinase Inhibition

In a final reaction volume of 25 µL, Abl (human) (5-10 mU) is incubated with 8 mM MOPS pH 7.0, 0.2 mM EDTA, 50 µM EAIYAAPFAKKK, 10 mM Mg(OAc)$_2$ and [γ-$^{33}$P-ATP] [specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

Results for the representative compounds of Formula I are provided in Table-2.

TABLE 2

Comparative potencies of tyrosine kinase inhibitors in c-Abl IC$_{50}$ (nM)

| I.a | I.b | Nilotinib | Ponatinib | Dasatinib | Imatinib |
|---|---|---|---|---|---|
| 0.9 | 0.6 | 18 | 0.4 | 0.27 | 190 |

Example 2

Brain/Plasma Pharmacokinetic Studies

To determine whether the compound of Formula I.a crosses the blood-brain barrier, C57BL6 mice were administered orally at 30 mg/kg of the compound of Formula I.a, 100 mg/kg of nilotinib or 30 mg/kg of dasatinib. At 1, 4 & 8 hour time points post treatment, mice were anesthetized with isoflurane and a 0.4 mL of blood was withdrawn from retro-orbital plexus into eppendorf tubes containing 8 µL sodium heparin as an anticoagulant (100 IU/ml) and transferred to ice containers. Blood samples were centrifuged immediately for 7 min at 8500 rpm, 4° C. Plasma was separated in the pre-labeled eppendorf tubes and stored at −70° C. till further analysis. Immediately thereafter, the mice were sacrificed, whole brain was removed and rinsed with ice-cold phosphate buffered saline (PBS) to remove extraneous blood and blot-dried. Brain tissue samples were weighed and homogenized in 1:2 volume of PBS using a tissue homogenizer and stored in labeled vials at −70° C. until further analysis. Concentrations of the compound of Formula I.a in brain and plasma were determined using the LC-MS technique.

Brain to plasma ratio was found to be significantly higher for the compound of Formula I.a as compared to that for nilotinib or dasatinib (see Table 3).

TABLE 3

Concentration of compounds in Brain and Plasma.

| Compounds | Treatment* (mg/kg) | Time points (hr) | Plasma conc. (ng of compound/mL of plasma) | Brain conc. (ng of compound/g of brain tissue) | Ratio of brain conc./plasma conc. |
|---|---|---|---|---|---|
| Compound of Formula I.a | 30 | 1 | 4798 ± 858 | 1901 ± 959 | 0.40 |
|  |  | 4 | 3167 ± 50 | 510 ± 367 | 0.16 |
|  |  | 8 | 2715 ± 379 | 435 ± 157 | 0.16 |
| Nilotinib | 100 | 1 | 31683 ± 7958 | 380 ± 70 | 0.01 |
|  |  | 4 | 38813 ± 11635 | 487 ± 126 | 0.01 |
|  |  | 8 | 16988 ± 2133 | 180 ± 46 | 0.01 |
| Dasatinib | 30 | 1 | 553 ± 550 | 23.4 ± 0 | 0.04 |
|  |  | 4 | 222 ± 122 | 25 ± 5 | 0.11 |
|  |  | 8 | BQL | 24 ± 4 | — |

BQL—below the limit of quantification

Example 3

Efficacy in Animal Model of Parkinson's Disease for Compound of Formula I.a C57BL/6 mice (6-8 weeks old, 25-30 g body weight) were administered orally with vehicle, the compounds of Formula I.a (10 or 30 mg/kg, once a day) for 7 days. On day 7, these animals received four intraperitoneal injections of a neurotoxin, 1-methyl-4-phenyl-1,2,3,6-tetrahydropyridine (MPTP-HCl; 17 mg/kg free base; Sigma) in saline at 2 hour intervals. Daily dosing with compound continued for 7 additional days after the last injection of MPTP. Briefly, the compound was administered 6 days prior to MPTP administration, on the day of MPTP administration and 7 days after MPTP administration. All animals were sacrificed 7 days after the MPTP administration and brain tissues were processed for immunohistochemistry evaluation. The standard avidin-biotin method (Benno et al., Brain Res., 1982; 246: 225-236) was used for the immunohistochemical detection of tyrosine hydroxylase (TH). Initially, the brains were sectioned at the substantia nigra pars compacta (SNPc) level using a cryostat and mounted on glass slides. The slides with brain sections were rinsed 3×5 minutes in 0.1 M PBS. The sections were first incubated for 30 minutes at room temperature with normal blocking serum in 0.1 M PBS with 0.3% Triton X-100 and for additional 2 hours with a rabbit polyclonal antibody to mouse tyrosine hydroxylase (Invitrogen) diluted 1:1000 in 0.1 M PBS with normal blocking serum. The slides with sections were further rinsed 3×5 minutes in 0.1 M PBS and incubated for 1 hour at room temperature with a biotinylated anti-rabbit antibody (Vectastain® ABC kit). The sections were rinsed 3×5 minutes in 0.1 M PBS and incubated for 1 hour at room temperature with A and B solutions (Vectastain® ABC kit) diluted 1:50 in 0.1 M PBS. After 1 hour the sections were rinsed 3×5 minutes in 0.1 M PBS and incubated in the 3,3'-diaminobenzidine (DAB)/$H_2O_2$ solution (Sigma) for approximately 5-8 minutes (the development process was checked under microscope for an optimal signal-to-noise ratio). The sections were first rinsed 2×5 minutes in 0.1 M PBS and then with 3×5 minutes in Milli-Q water. The slides were cover slipped in glycerol-gelatin solution and kept at room temperature overnight for drying after which images of the stained brain sections were captured using a camera attached to a microscope and anaslyzed using NIH ImageJ® software (NIH, Bethesda, Md.). Images were analyzed by converting to 8-bit resolution and optimal brightness/contrast. Background and pseudo signals on individual images were removed and area covered by cell bodies and fibers was measured. Percentage area compared to total image area and integrated density was calculated. Results obtained were compared for any inter-group or intra-group variation and statistical significance using GraphPad Prism® 6.0. Oral administration of the compound of Formula I.a significantly prevented the neurodegeneration induced by MPTP as seen from photomicrographs from coronal sections showing TH-positive neurons (FIG. 1), the determination of percentage area of TH-positive neurons (FIG. 2) and integrated density of TH-immunoreactivity (FIG. 3)

Example 4

Efficacy in Animal Model of Parkinson's Disease for Compound of Formula I.b Efficacy of compound of Formula I.b for treating the Parkinson's disease was tested by the same method as described for the compound of Formula I.a in Example 3 above.

The results obtained were compared for any inter-group or intra-group variation and statistical significance using GraphPad Prism® 6.0. Oral administration of the compound of Formula I.b significantly prevented the neurodegeneration induced by MPTP as seen from photomicrographs from coronal sections showing TH-positive neurons (FIG. 4), the determination of percentage area of TH-positive neurons (FIG. 5) and integrated density of TH-immunoreactivity (FIG. 6)

Example 5

Electrophysiological Procedures—Effect on hERG $K^+$ Channel

The compound of Formula I.a and I.b were tested for cardiovascular safety in an in vitro test to determine inhibition of hERG $K^+$ channel. The compounds of Formula I.a and I.b did not show any significant inhibition of hERG current at the concentration tested.

The in vitro effect of the compounds of Formula I.a and I.b on ionic currents in voltage-clamped human embryonic kidney cells (HEK293) that stably express the human ether-à-go-go-related gene (hERG) was examined. Two concentrations of the compounds of Formula I.a and I.b (1 and 10 µM) were tested at near physiological temperature.

Cells were transferred to the recording chamber and superfused with vehicle control solution (HEPES-buffered physiological saline solution+1% dimethylsulfoxide+1% Bovine serum albumin). Micropipette solution for whole cell patch clamp recordings was composed of: potassium aspartate, 130 mM; $MgCl_2$, 5 mM; EGTA, 5 mM; ATP, 4 mM; HEPES, 10 mM; pH adjusted to 7.2 with 10N KOH. Micropipette solution was prepared in batches, aliquoted, stored frozen and a fresh aliquot thawed each day. The recording was performed at a temperature of 33 to 35° C. using a combination of in-line solution pre-heater, chamber heater and feedback temperature controller. Temperature was measured using a thermistor probe in the recording chamber. Micropipettes for patch clamp recording were made from glass capillary tubing using a P-97 micropipette puller (Sutter Instruments, Novato, Calif.). A commercial patch clamp amplifier was used for whole cell recordings. Before digitization, current records were low-pass filtered at one-fifth of the sampling frequency.

Cells stably expressing hERG were held at −80 mV. Onset and steady state inhibition of hERG potassium current due to the test compounds (Formula I.a and I.b) were measured using a pulse pattern with fixed amplitudes (conditioning prepulse +20 mV for 1 s; repolarizing test ramp to −80 mV (−0.5 V/s) repeated at 5 s intervals). Each recording ended with a final application of a supra-maximal concentration of the reference substance (E-4031, 500 nM) to assess the contribution of endogenous currents. The remaining uninhibited current was subtracted off-line digitally from the data to determine the potency of the test compounds for hERG inhibition.

The compound of Formula I.a inhibited hERG current by (Mean±SEM) 2.1±0.4% at 1 μM (n=3) and 9.7±0.4% at 10 μM (n=3) compared to 1.0±0.6% (n=3) in vehicle control (see Table 4). Concentrations of the compound of Formula I.a greater than 10 μM were not tested due to the solubility limit of the compound in the vehicle control. Under similar conditions, the positive control (terfenadine, 60 nM) inhibited hERG potassium current by (Mean±SD; n=2) 82.8±1.2%, confirming a slight effect of the compound of Formula I.a at its very high concentration in hERG $K^+$ channel. In comparison nilotinib shows nearly 90% inhibition at 1 μM concentration (Table 5).

TABLE 4

Mean percent inhibition of hERG current at each concentration of the compound of Formula I.a and I.b.

| Compound | Concentration (μM) | Mean | SD | SEM | N |
|---|---|---|---|---|---|
| Compound I.a | 0 | 1.0% | 1.0% | 0.6% | 3 |
|  | 1 | 2.1% | 0.7% | 0.4% | 3 |
|  | 10 | 9.7% | 0.7% | 0.4% | 3 |
| Compound I.b | 0 | 1.6% | 0.3% | 0.2% | 3 |
|  | 0.3 | 5.6% | 1.3% | 0.8% | 3 |
|  | 1 | 12.9%* | 4.1% | 2.4% | 3 |
|  | 3 | 25.0%* | 6.0% | 3.4% | 3 |

*Value is statistically different from vehicle alone.

TABLE 5 percentage inhibition of hERG current by nilotinib[#]

| Conc. (μM) | 0.03 | 0.1 | 0.3 | 1 |
|---|---|---|---|---|
| % Inhibition | 14.9 ± 2 | 43.9 ± 0.7 | 70.4 ± 2.5 | 89.7 ± 1.6 |

[#]Data from CDER pharmacological review for NDA No. 22-068 (Tasigna ® Capsule) pg No. 31

Example 6

Effect of Compound of Formula I.a on QT, $QT_c$ Intervals, and Heart Rate in Conscious Beagle Dogs The compound of Formula I.a was subjected to in vivo test to determine its effect on the QT, $QT_{cb}$ & $QT_{cf}$ intervals, and heart rate in conscious beagle dogs.

Compound of Formula I.a was administered via peroral (p.o.) route at three dose levels: 5, 15, and 30 mg/kg in conscious telemetered male and female beagle dogs. Emesis occurred in two animals (1 male and 1 female) treated with the 30 mg/kg dose group of the compound of Formula I.a at 14 min following dosing. Hence, the group treated with 30 mg/kg dose was not considered for the data analysis. No emesis was observed with 5 and 15 mg/kg doses.

Measurements of ECG parameters (QT interval, $QT_{cb}$ interval, $QT_{cf}$ interval) and heart rate were carried out and recorded over a period of 2 hour prior to drug administration (baseline), and continuously up to 24 hour post-administration. Each animal received both vehicle (placebo) and three different doses of the compound of Formula I.a on different days in a Latin square design, with a washout period of a minimum of 96 hr. On a separate day, one additional oral dosing of compound of Formula I.a was performed to assess plasma concentrations of the compound of Formula I.a at different time points, to derive pharmacokinetic (PK) parameters.

Data of ECG parameters (QT interval, $QT_{cb}$ interval, $QT_{cf}$ interval,) and heart rate were statistically compared as follows: Data of the placebo group at 0.5, 1, 1.5, 2, 3, 4, 5, 6, 8, 12, and 24 hour time points were compared with baseline data of the same group. Data of different groups treated with the compound of Formula I.a were compared with the corresponding data of the placebo group.

Analysis of ECG based on pooled data of male and female dogs showed that as compared to baseline, placebo treatment had no statistically significant effect on any of the ECG parameters (QT interval, $QT_{cb}$ interval, $QT_{cf}$ interval) and heart rate. Compound of Formula I.a at 5 and 15 mg/kg doses had no effects on QT, $QT_{cb}$, $QT_{cf}$, durations compared with placebo. In addition, other parameter such as heart rate remained unchanged.

The PK analysis showed a dose-dependent systemic exposure of the compound of Formula I.a to animals administered with different doses of the compound of Formula I.a. $AUC_{0-inf}$ was in the range of 1925 to 4824, 6776 to 12756, and 25927 to 46749 hr×ng/mL with 5, 15, and 30 mg/kg doses of the compound of Formula I.a, respectively. $C_{max}$ was in the range of 1218 to 2033, 2723 to 5323, and 9825 to 9967 ng/mL with 5, 15, and 30 mg/kg doses of the compound of Formula I.a, respectively.

The results of this study showed that single oral administration of the compound of Formula I.a up to 15 mg/kg dose has no effect on cardiovascular functions in conscious beagle dogs. There was no change in ECG morphology at any dose levels of the compound of Formula I.a. There were no gender differences in the treatment effect on ECG parameters and heart rate.

Example 7

Effect of Compound of Formula I.b on QT, QTc Intervals, and Heart Rate in Anesthetized Guinea Pig The effect of compound of Formula I.b on QT, QTc intervals, and heart rate was studied in anesthetized guinea pig.

Male Dunkin-Hartley guinea pigs of body weight range 300-400 g were anaesthetized by intraperitoneal injection of urethane (1.5 g/kg). A tracheotomy was performed and animal was allowed to breath spontaneously throughout the experiment. The left jugular vein was catheterized using polyethylene catheter filled with heparinized saline solution (100 IU/mL) for drug administration. Electrodes were placed in lead II position and baseline ECG was recorded.

For different animals, according to body weight, doses of the compound of Formula I.b were weighed and prepared in 0.5 mL of DMSO and administered via a slow intravenous infusion administered over a period of 10 min. ECGs were recorded during and after completion of infusion up to 0.5 hr. QT and RR intervals were measured, using PowerLab 4SP® software. The data were analyzed at 1, 5, and 10 min during infusion and 5, 10, 15 and 30 min after infusion taking mean of 9 beats.

There was no change in QT intervals with administration of 1 mg/kg intravenous dose of the compound of Formula I.b.

The invention claimed is:

1. A method of treating Parkinson's disease in a subject comprising administering a therapeutically effective amount of a compound of Formula I

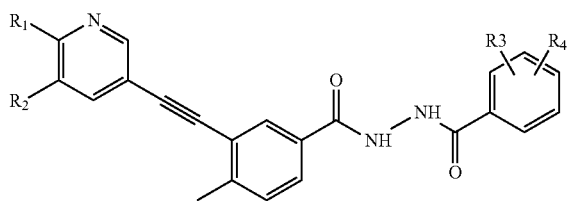

Formula I wherein, $R_1$ is —NHC(O) $C_{3-6}$ cycloalkyl and $R_2$ is hydrogen;

or $R_1$ and $R_2$ along with the carbon atoms to which they are attached form a six membered aromatic ring, wherein the ring is substituted with one or more groups selected from hydrogen, halogen and $C_{1-6}$ alkyl;

$R_3$ and $R_4$ are independently selected from group comprising hydrogen, halogen, $C_{1-3}$ alkyl, $OC_{1-3}$ alkyl, $NO_2$, $SC_{1-3}$ alkyl, $C_{1-3}$ haloalkyl, $OC_{1-3}$ haloalkyl, and $SC_{1-3}$ haloalkyl, and wherein the compound of Formula I exhibits a ratio of concentration in brain to concentration in plasma of more than 0.15, and does not result in change in QT interval in the subject.

2. The method as claimed in claim 1, wherein $R_1$ in the compound of Formula I is —NHC(O) cyclopropyl and $R_2$ is hydrogen.

3. The method as claimed in claim 2, wherein $R_1$ and $R_2$ in the compound of Formula I, along with the carbon atoms to which they are attached form a six membered aromatic ring, wherein the ring is substituted with one or more groups selected from hydrogen, halogen and $C_{1-6}$ alkyl.

4. The method as claimed in claim 2, wherein $R_1$ and $R_2$ in the compound of Formula I, along with the carbon atoms to which they are attached form a six membered aromatic ring, wherein the ring is substituted with hydrogen; and $R_3$ is chloro and $R_4$ is methyl and are present as a substituent at 2 and 6 position in the ring.

* * * * *